(12) United States Patent
Van Bommel et al.

(10) Patent No.: US 12,345,396 B2
(45) Date of Patent: Jul. 1, 2025

(54) TRACK LIGHTING SYSTEM

(71) Applicant: SIGNIFY HOLDING B.V., Eindhoven (NL)

(72) Inventors: Ties Van Bommel, Horst (NL); Robert Jacob Pet, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/832,955

(22) PCT Filed: Jan. 19, 2023

(86) PCT No.: PCT/EP2023/051205
§ 371 (c)(1),
(2) Date: Jul. 25, 2024

(87) PCT Pub. No.: WO2023/143998
PCT Pub. Date: Aug. 3, 2023

(65) Prior Publication Data
US 2025/0109842 A1 Apr. 3, 2025

(30) Foreign Application Priority Data
Jan. 27, 2022 (EP) .................................... 22153624

(51) Int. Cl.
*F21V 21/35* (2006.01)
*A61L 9/20* (2006.01)
(Continued)

(52) U.S. Cl.
CPC ............... *F21V 21/35* (2013.01); *A61L 9/20* (2013.01); *F21V 21/30* (2013.01); *H05B 47/115* (2020.01);
(Continued)

(58) Field of Classification Search
CPC .......... F21V 21/35; F21V 21/30; F21V 21/34; H05B 47/115; A61L 9/20; F21Y 2113/10; F21Y 2115/10; F21Y 2113/30
See application file for complete search history.

(56) References Cited

U.S. PATENT DOCUMENTS

| 5,772,315 A | * | 6/1998 | Shen | ...................... F21V 21/35 |
| | | | | 362/396 |
| 10,539,308 B2 | * | 1/2020 | Bernard | .................. F21V 21/35 |

(Continued)

FOREIGN PATENT DOCUMENTS

| CN | 202419518 U | 9/2012 |
| CN | 204213665 U | 3/2015 |

(Continued)

*Primary Examiner* — Bao Q Truong (57) ABSTRACT

A track lighting system 100, comprising a power track 110 and a LED module 130. The LED module comprises a first LED light source 140 and a first housing 150, wherein the first housing comprises a first collimator 160 having a principal axis, E, collimating the first LED light in a first direction, $D_1$. The LED module further comprises a second LED light source 170, and a second housing 180, wherein the second housing comprises a second collimator 190 having a second principal axis, F, collimating the second LED light in a second direction, $D_2$. The first collimator is tiltable with respect to a normal, C, such that the first principal axis, E, forms a first angle, $\alpha$, with respect to the normal, C. The second principal axis, F, of the second collimator is fixed with respect to tilt at a second angle, $\beta$, with respect to the normal, C.

14 Claims, 3 Drawing Sheets

(51) Int. Cl.
    *F21V 21/30*     (2006.01)
    *H05B 47/115*     (2020.01)
    *F21Y 113/00*     (2016.01)
    *F21Y 113/10*     (2016.01)
    *F21Y 115/10*     (2016.01)

(52) U.S. Cl.
    CPC ........ *F21Y 2113/10* (2016.08); *F21Y 2113/30* (2023.05); *F21Y 2115/10* (2016.08)

(56) References Cited

U.S. PATENT DOCUMENTS

| | | |
|---|---|---|
| 2018/0180226 A1 | 6/2018 | Van Bommel et al. |
| 2019/0024874 A1 | 1/2019 | Van Bommel et al. |
| 2020/0056767 A1 | 2/2020 | Shih |
| 2021/0278061 A1 | 9/2021 | Ben-Shmuel et al. |
| 2022/0016284 A1 | 1/2022 | Portinga et al. |

FOREIGN PATENT DOCUMENTS

| | | |
|---|---|---|
| CN | 211551303 U | 9/2020 |
| DE | 20009450 U1 | 8/2000 |
| DE | 202021101450 U1 | 4/2021 |
| EP | 2413028 A2 | 2/2012 |
| WO | 2021134533 A1 | 7/2021 |

\* cited by examiner

TRACK LIGHTING SYSTEM

CROSS-REFERENCE TO PRIOR APPLICATIONS

This application is the U.S. National Phase application under 35 U.S.C. § 371 of International Application No. PCT/EP2023/051205, filed on Jan. 19, 2023, which claims the benefit of European Patent Application No. 22153624.6, filed on Jan. 27, 2022. These applications are hereby incorporated by reference herein.

FIELD OF THE INVENTION

The present invention generally relates to the field of lighting systems. More specifically, the present invention relates to a track lighting system comprising light-emitting diodes (LED).

BACKGROUND OF THE INVENTION

The use of light emitting diodes (LED) for illumination purposes continues to attract attention. Compared to incandescent lamps, fluorescent lamps, neon tube lamps, etc., LEDs provide numerous advantages such as a longer operational life, a reduced power consumption, and an increased efficiency related to the ratio between light energy and heat energy. In particular, LED filament lamps are highly appreciated as they are very decorative.

It is of interest to combine the advantageous properties of LEDs according to the above with the advantageous properties of disinfection (bactericidal) lighting. It will be appreciated that disinfection lighting has become a topic and a trend of renewed interest as the demand for sterilization increases. For example, the use of ultraviolet light, UVC, can be used for disinfection purposes, e.g. inactivating bacteria.

Another trend is track lighting, being a lighting system in which luminaires are fitted on and electrically connected to a track, allowing variable positioning along the track. Lighting arrangements such as spotlights in some examples in the prior art may be arranged via suspended tracks arranged in the ceiling for an improved directionality of the light during operation.

Hence, it is of interest to provide a track lighting device or system, preferably provided with LEDs, which furthermore can provide disinfection lighting. However, if such a track lighting system is arranged in a ceiling, e.g. as a spotlight, it should be noted that only upper air disinfection is desired for safety reasons.

SUMMARY OF THE INVENTION

It is an object of the present invention to mitigate the above problems and to provide a lighting device which can provide lighting both for illumination and disinfection purposes, whilst at the same time ensuring that persons in a space wherein the lighting device is arranged are not (directly) subjected to lighting for disinfection purposes.

This and other objects are achieved by a lighting arrangement having the features in the independent claim. Preferred embodiments are defined in the dependent claims.

Hence, according to the present invention, there is provided a track lighting system, comprising a power track being connectable to an electric supply and arranged to be mountable to a surface in a mounting direction, B, and a first light-emitting diode, LED, module being electrically and mechanically connectable to the power track. The first LED module comprises a first LED light source arranged to emit first LED light and a first housing, wherein the first housing at least partially encloses the first LED light source, and wherein the first housing comprises a first collimator having a first principal axis, E, and arranged to collimate the first LED light in a first main direction, $D_1$. The first LED module further comprises a second LED light source arranged to emit second LED light, wherein the second LED light is different from the first LED light, a second housing, wherein the second housing at least partially encloses the second LED light source, wherein the second housing comprises a second collimator having a second principal axis, F, and arranged to collimate the second LED light in a second main direction, $D_2$. The first collimator is tiltable with respect to a normal, C, of a plane, A, wherein the normal, C, is in an opposite direction to the mounting direction, B, such that the first principal axis, E, forms a first angle, $\alpha$, with respect to the normal, C. The second principal axis, F, of the second collimator is fixed with respect to tilt at a second angle, $\beta$, with respect to the normal, C.

Thus, the present invention is based on the idea of providing a track lighting system which can provide light for both illumination purposes and disinfection purposes whereas the lighting arrangement is arranged such that omnidirectional light may be provided for illumination purposes, whereas allowable directions of the beam of the light for disinfection purposes are limited. As this disinfection function aims at upper room disinfection it is of importance that the bean of light for the disinfection purposes is only present in the upper part of the room. Therefore, the main direction of the disinfection light should have a tilt at a second angle, $\beta$, chosen in the range between 70° and 110°. It will be preferred to have the disinfection light to have an even smaller range for the tilt angle preferably between 80° and 100° and most preferably between 85° and 95°. This limitation will therefore only allow indirect exposure of light for disinfection purposes to people occupying a space where the track lighting system resides.

It will be appreciated that the track lighting system allows variable positioning along the track. This entails the lighting system to be adaptable to different lighting needs and/or desires regarding e.g. providing light to a specific area in a larger space wherein the track lighting system is arranged.

The present invention is further advantageous in that the first collimator is tiltable with respect to the normal, C, of the plane, A. This provides the lighting system to be further adaptable regarding different lighting needs, requirements and/or desired settings as well as being aesthetically attractive.

It should also be noted that the second collimator is fixed with respect to tilt with respect to the normal, C. This may reduce the risk of uncontrolled light reflection from the second collimator. The fixation of the second collimator with respect to the normal, C, is further advantageous in that it may reduce direct exposure of light from the second collimator for persons in a space wherein the lighting arrangement is arranged.

According to the present invention, there is provided a track lighting system comprising a power track being arranged to be mountable to a surface in a mounting direction, B. By the term "mounting direction", it is here meant a direction towards a surface, the direction being perpendicular to said surface. The first light-emitting diode, LED, module comprises a first LED light source arranged to emit first LED light and a second LED light source arranged to emit second LED light, wherein the second LED light is different from the first LED light. By "different" it is here meant that at least one property of the first LED light source is not shared with the second LED light source such as different wavelengths. The track lighting system further comprises a second collimator having a second principal axis, F. This second principal axis, F, is fixed with respect to tilt at a second angle, $\beta$, with respect to the normal, C. By "fixed" it is here meant that it is not possible to change the tilt of the principal axis, F.

According to an embodiment of the present invention, the second collimator may be rotatable, wherein the normal, C, is the rotation axis. Hence, the second collimator, which has a second principal axis, F, is rotatable around the normal, C, which hereby constitutes the rotation axis. The present embodiment is advantageous in that the second collimator, and therefore also the emission beam from the second collimator, can be rotated, reaching a larger area of the space the track lighting system resides in and, sequentially, enabling a larger area to be disinfected. It will be appreciated that the second collimator, via the rotation, may be oriented (set) in a specific direction, which is advantageous in case there is a wish and/or need to provide disinfection in a specific area.

According to an embodiment of the present invention, the second collimator may be arranged such that the second principal axis, F, is arranged perpendicular to the normal, C. The present embodiment is particularly advantageous in that the risk of uncontrolled UV reflection is reduced from e.g. a ceiling whereon the track lighting system may be mounted.

According to an embodiment of the present invention, at least one of the first collimator and the second collimator may be rotatably arranged around the normal, C. In other words, the first and/or the second collimator may be rotatably arranged around the normal, C. The present embodiment is advantageous as in that the first and/or the second collimator may be rotatably arranged around the normal, C, and therefore the respective emission beams would be rotatably arranged accordingly. This may increase the versatility of the orientation of the light emitted from the track lighting system. Therefore, said embodiment of the present invention may facilitate different lighting needs, such that e.g. delivering light to a specific area in a larger space where the track lighting system resides.

According to an embodiment of the present invention, the track lighting system may comprise a locking mechanism configured to lock an orientation of the second collimator around the normal, C. The present embodiment is further advantageous in that the orientation around the normal, C, of the emission beam from the second collimator can be locked, ensuring that a specific orientation around the normal, C, of the second collimator remains unless the lock is removed. Consequently, if the lock is removed, the second collimator can again be oriented around the normal, C. The locking mechanism therefore further reduces the risk of uncontrolled UV reflection, ensuring the second collimator to be arranged in a safe position regarding persons within the area of the lighting system such that the exposure of the UV light is not direct.

According to an embodiment of the present invention, the first LED light may be white light having a correlated color temperature, CCT, in a range from 2000 to 8000 K and a color rendering index, CRI, of at least 70.

According to an embodiment of the present invention, the second LED light may at least be one of violet and ultraviolet, UV, light. Hence, the second LED light may be violet and/or ultraviolet, UV, light. For example, the UV light may have a wavelength≤380 nm. For example, the violet light may have a wavelength 380-420 nm. The present embodiment is advantageous in that violet and ultraviolet light are effective for disinfection purposes.

According to an embodiment of the present invention, the second LED light may be ultraviolet C, UVC, light i.e. a wavelength<285 nm. The present embodiment is particularly advantageous as UVC light is the most effective wavelength for inactivating viruses. This usage of UVC light in the lighting system of the present invention can therefore effectively prevent the spread of viruses in spaces wherein the lighting system is arranged, even whilst the space is occupied with e.g. people. In a preferred embodiment, the second LED light may be far-UVC, light i.e. a wavelength 190-230 nm. Far-UVC light is less harmful than UVC light with a longer wavelength, such as near-UVC light i.e. a wavelength 230-285 nm.

According to an embodiment of the present invention, a projection, P, of the first main direction, $D_1$, in the plane, A, and the second main direction, $D_2$, may be parallel, and wherein the first main direction, $D_1$, may form a third angle, $\gamma$, with the second main direction, $D_2$. Hence, the first main direction, $D_1$, in the plane, A, and the second main direction, $D_2$, may lie in a same plane, G, whereas the plane, G, is perpendicular to plane A. The present embodiment is advantageous as the respectively emission beams from the first LED light source and the second LED light source may both lie in the plane, G. This would entail providing both the light source for illumination purposes and the light source for disinfection purposes in the same direction as the plane, G. Therefore, said embodiment of the present invention may provide different lighting needs, such that e.g. delivering light, both for illumination purposes and for disinfection purposes, to a specific area in a larger space where the track lighting system resides.

According to an embodiment of the present invention, the collimated first LED light may have a first full width at half maximum, $FWHM_1$, and the collimated second LED light may have a second full width at half maximum, $FWHM_2$, wherein $FWHM_1 > FWHM_2$. In other words, the emission beam spread of the collimated first LED light may be wider than the emission beam spread of the collimated second LED light. The present embodiment is advantageous in that the light source for illumination purposes may reach a larger area of the space the track lighting system resides in, and, consequently, illuminating a larger area. The present embodiment is further advantageous in that the emission beam spread of the light source for disinfection purposes may be more narrow than the emission beam spread of the light source for illumination purposes, enabling that a more distinct area is disinfected. Additionally, the present embodiment is advantageous as a narrow $FWHM_2$ may reduce the risk of uncontrolled UV reflection, making it safer in regard to persons within said space.

According to an embodiment of the present invention, $FWHM_2$ may be <5° in a direction perpendicular to the normal, C. The present embodiment is advantageous in that the collimated second LED light may disinfect a distinct area of the space the track lighting system resides in without being directed towards occupants within said space. Preferably, $FWHM_2$ may be <4°, more preferably $FWHM_2$ may be <3°, and most preferably $FWHM_2$ may be <2°. Additionally, the present embodiment is advantageous as a narrow $FWHM_2$ may reduce the risk of uncontrolled UV reflection, making it safer in regard to persons within said space.

According to an embodiment of the present invention, there is provided a track lighting system according to any one of the previously described embodiments. The track lighting system may comprise a control unit configured to control the second LED light source, and at least one sensor coupled to the control unit, wherein the at least one sensor is configured to detect at least one of at least one object and at least one person, and, in case at least one of the at least one object and the at least one person is detected, to generate a sensor signal and send the generated signal to the control unit. The control unit is configured to control the second LED light source based on the sensor signal received from the at least sensor. Hence, the control unit may control the second LED light source, and the track lighting system may further comprise a sensor, wherein the sensor is configured to detect an object and/or a person. In case an object is detected, the sensor may generate a sensor signal and send the generated signal to the control unit, whereas the control unit is configured to control the second LED light source based on the sensor signal received from the sensor. According to the present embodiment, the second LED light source may be violet and/or ultraviolet light, or ultraviolet C light. The present embodiment is advantageous in that if detecting an object, the control unit may control the second LED light source. This may reduce the risk of uncontrolled light reflection due to e.g. blocking object. Furthermore, the direct exposure of lighting may be reduced for persons in a space wherein the lighting device is arranged.

According to an embodiment of the present invention, there is provided a track lighting system. The track lighting system may comprise a user interface configured to control only the first LED light source. In other words, the user interface provides a way for a user to interact with the first LED light. According to the present embodiment, the second LED light source may be violet and/or ultraviolet light, or ultraviolet C light. The present embodiment is particularly advantageous in that the user interface enables the user to adjust the first LED light according to different lighting needs and/or desires regarding e.g. increasing or decreasing the luminosity of the first LED light source.

According to an embodiment of the present invention, there is provided a track lighting system according to any one of the previously described embodiments. The track lighting system may comprise a blocking mechanism configured to avoid the first housing blocking the collimated second LED light. Hence, the blocking mechanism ensures that the emission beam of the collimated second LED light may radiate unhindered relative blockage from the first housing. The present embodiment is advantageous in that the risk of uncontrolled UV reflection, due to the first housing blocking the emission beam from the collimated second LED light, is reduced.

According to an embodiment of the present invention, there is provided a track lighting system according to any one of the preceding claims, further comprising at least one second light-emitting diode, LED, module being electrically and mechanically connectable to the power track. The at least one second LED module comprises a third LED light source arranged to emit third LED light, a third housing, wherein the third housing at least partially encloses the third LED light source, and wherein the third housing comprises a third collimator arranged to collimate having a third principal axis, E, and arranged to collimate the third LED light in a third main direction, $D_3$. The at least one second LED module further comprises a fourth LED light source arranged to emit fourth LED light, wherein the fourth LED light is different from the first LED light, a fourth housing, wherein the fourth housing at least partially encloses the fourth LED light source, wherein the fourth housing comprises a fourth collimator having a fourth principal axis, F, and arranged to collimate the fourth LED light in a fourth main direction, $D_4$. The third collimator is tiltable with respect to a normal, C, of a plane, A, wherein the normal, C, is in an opposite direction to the mounting direction, B, such that the third principal axis, E, forms a first angle, $\alpha$, with respect to the normal, C. The fourth principal axis, F, of the fourth collimator is fixed with respect to tilt at a second angle, $\beta$, with respect to the normal, C. The third LED light is white light having a correlated color temperature, CCT, in a range from 2000 to 8000 K and a color rendering index, CRI, of at least 70, wherein the fourth LED light is at least one of violet and ultraviolet, UV, light. A projection, P, of the third main direction, $D_3$, in the plane, A, and the fourth main direction, $D_4$, are parallel, and wherein the third main direction, $D_3$, forms a third angle, $\gamma$, with the fourth main direction, $D_4$.

Further objectives of, features of, and advantages with, the present invention will become apparent when studying the following detailed disclosure, the drawings and the appended claims. Those skilled in the art will realize that different features of the present invention can be combined to create embodiments other than those described in the following.

BRIEF DESCRIPTION OF THE DRAWINGS

This and other aspects of the present invention will now be described in more detail, with reference to the appended drawings showing embodiment(s) of the invention.

DETAILED DESCRIPTION

Figure 1:
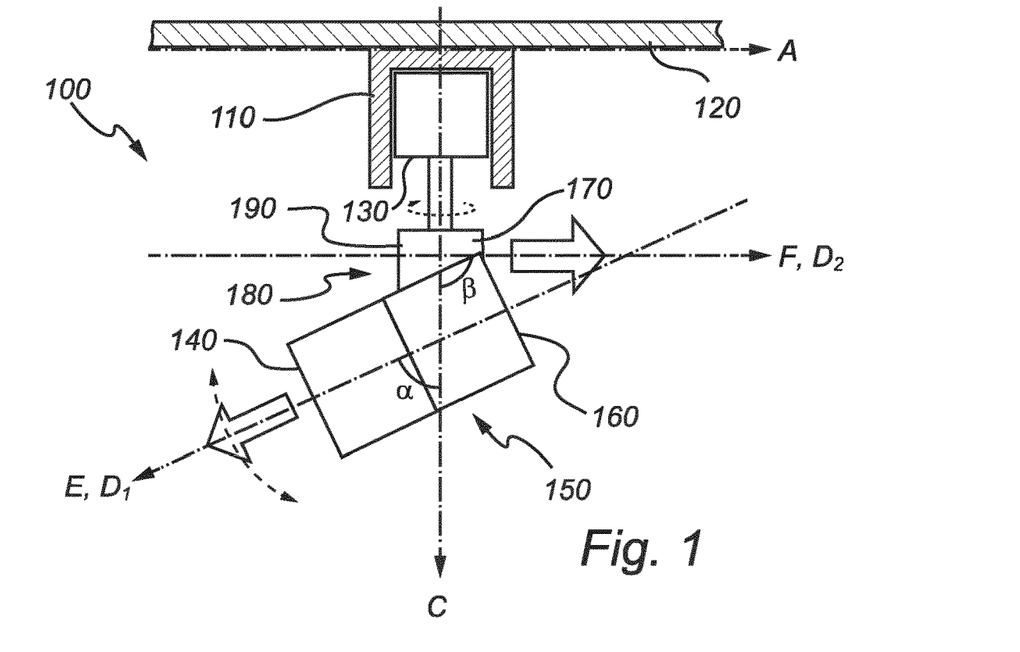
FIG. 1 is a schematic view of a track lighting system according to an exemplifying embodiment of the present invention, where the first collimator is tiltable with respect to the normal, C, and where the second collimator is arranged such that the second principal axis, F, is arranged perpendicular to the normal, C.

FIG. 1 is a schematic view of a track lighting system 100 according to an exemplifying embodiment of the present invention.

The track lighting system 100 in FIG. 1 comprises a power track 110. The power track 110 is arranged to be mountable to a surface 120, wherein the surface 120 may constitute e.g. a ceiling, a vertical wall or a wall being inclined with respect to a ceiling (e.g. that the wall is inclined 0-90° with respect to the ceiling). The power track 110 is arranged to be mountable to the surface 120 in a mounting direction, B (not shown), where the mounting direction is a direction towards the surface 120, the direction being perpendicular to said surface 120. According to the arrangement of FIG. 1, the power track 110 is mounted to a ceiling. The power track 110 is connectable to an electric supply. The power track 100 may have a U-shape in a cross-section transversal to a longitudinal extension of the power track, and wherein the power track has a length, L, a width, W, and a height, H, wherein L>25·W, and L>25·H and 0.2<H/W<5.

The track lighting system 100 further comprises a first light-emitting diode, LED, module 130. The first LED module 130 is electrically and mechanically connectable to the power track 110. The first LED module 130 is slidably arranged with respect to the power track 110.

The LED module 130 comprises a first LED light source 140 arranged to emit first LED light. The LED module 130 further comprises a first housing 150 which partially encloses the first LED light source 140. According to this example, the first housing 150 has the shape of a cylinder. The first housing 150 comprises a first collimator 160 which has a first principal axis, E. The first collimator 160 is arranged to collimate the first LED light in a first main direction, $D_1$. The first collimator 160 is tiltable with respect to a normal, C, of a plane, A. The normal, C, is in an opposite direction to the mounting direction, B, in such a way that the first principal axis, E, forms a first angle, α, with respect to the normal, C.

The LED module 130 further comprises a second LED light 170 arranged to emit second LED light. The LED module 130 further comprises a second housing 180 which partially encloses the second LED light source 170. According to this example, the second housing 180 has the shape of a cylinder. The second housing 180 comprises a second collimator 190 which has a second principal axis, F. The second collimator 190 is arranged to collimate the second LED light in a second main direction, $D_2$. The second collimator 160 is fixed with respect to the normal, C, such that the second principal axis, F, forms a second angle, β, with respect to the normal, C. According to the arrangement in FIG. 1, the second collimator 190 is arranged such that the second principal axis, F, is arranged perpendicular to the normal, C. Consequently, the second principal axis, F, is parallel to a horizontal axis. Hence, the emission beam from the second LED light source 170 is substantially oriented in a horizontal direction.

The disinfection function aims at upper room disinfection. Therefore, the main direction of the disinfection light has in this embodiment a tilt of 90°, that is it is directed in horizontal direction. Further, the tilt can be chosen in a certain range, amongst others, depending on the opening angle (FWHM) of the disinfection light. Preferably, the disinfection light should have tilt at a second angle, β, chosen in the range between 70° and 110°. It will be preferred to have the disinfection light to have an even smaller range for the tilt angle preferably between 80° and 100° and most preferably between 85° and 95°.

In case the track lighting system 100 is mounted to a ceiling via the power track 110, the (instantaneous) orientation of the track lighting system 100 as exemplified in FIG. 1 results in an emission of the first LED light in the first main direction, $D_1$, obliquely to the ceiling, and an emission of the second LED light in the second main direction, $D_2$, parallel to the ceiling.

Furthermore, according to FIG. 1, the first collimator 160 and/or the second collimator 180 are rotatably arranged around the normal, C. These rotations can occur independently or dependently in relation to the first and second collimators 160, 190.

Figure 2:
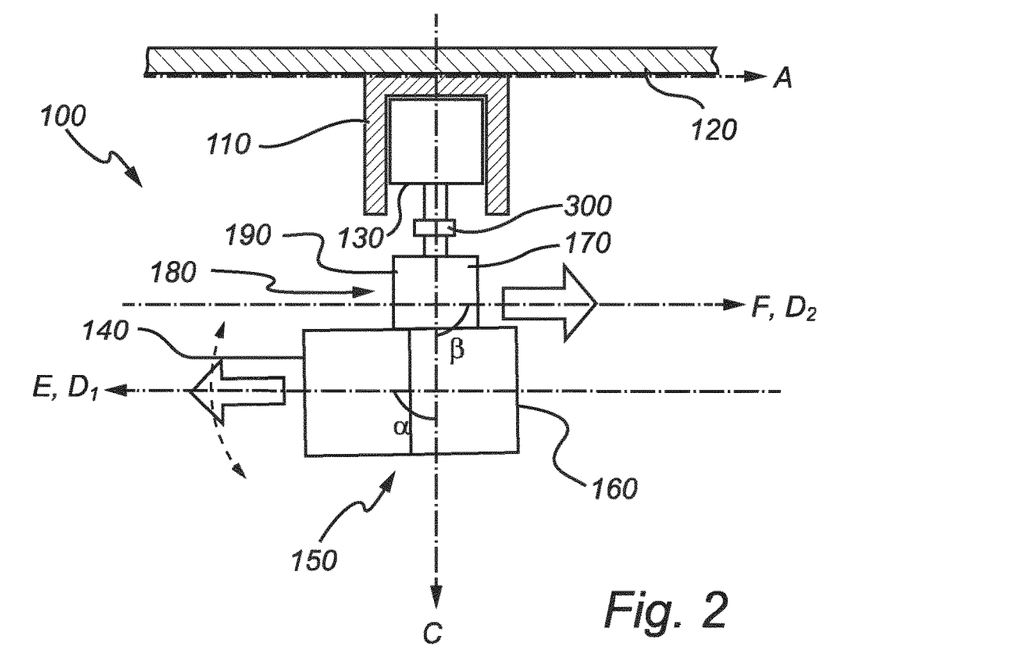
FIG. 2 is a schematic view of the track lighting system according to FIG. 1, with a locking mechanism configured to lock an orientation of the second collimator, where the first collimator is arranged such that the first principal axis, E, is parallel with the second principal axis, F.

FIG. 2 is a schematic view of a track lighting system 100 according to an exemplifying embodiment of the present invention. Regarding the features and/or functions of the track lighting system 100, it is referred to FIG. 1 for an increased understanding. According to the arrangement of FIG. 2, the first principal axis, E, of the first collimator 160 is parallel with the second principal axis, F, of the second collimator 190. Said arrangement is in an initial instance, and the first collimator 160 is continued tiltable with respect to the normal, C. In case the track lighting system 100 is mounted to a ceiling via the power track 110, the (instantaneous) orientation of the track lighting system 100 as exemplified in FIG. 2 results in an emission of the first LED light in the first main direction, $D_1$, parallel to the ceiling, and an emission of the second LED light in the second main direction, $D_2$, parallel to the ceiling.

The track lighting system 100 further comprises a locking mechanism 300, configured to lock an orientation of the second collimator 190 around the normal, C. The locking mechanism 300 ensures a specific orientation of the second collimator 160.

Figure 3:
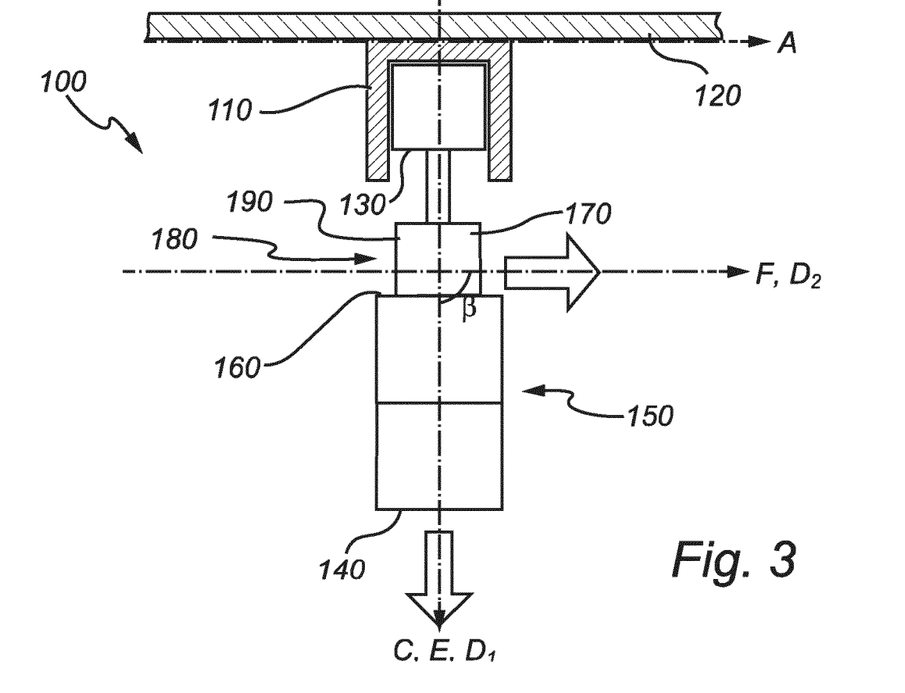
FIG. 3 is a schematic view of the track lighting system according to FIG. 1, where the first collimator is arranged such that the first principal axis, E, is perpendicular to the second principal axis, F.

FIG. 3 is a schematic view of a track lighting system 100 according to an exemplifying embodiment of the present invention. Regarding the features and/or functions of the track lighting system 100, it is referred to FIG. 1 for an increased understanding. According to the arrangement of FIG. 3, the first principal axis, E, of the first collimator 160 is perpendicular to the second principal axis, F, of the second collimator 190. According to this example, wherein the track lighting system 100 is mounted to a ceiling via the power track 110, the (instantaneous) orientation of the track lighting system 100 as exemplified results in an emission of the first LED light in the first main direction, $D_1$, downwards, e.g. into a room, whereas an emission of the second LED light in the second main direction, $D_2$, is parallel to the ceiling. Said arrangement is in an initial instance, and the first collimator 160 is continued tiltable with respect to the normal, C.

Figure 4:
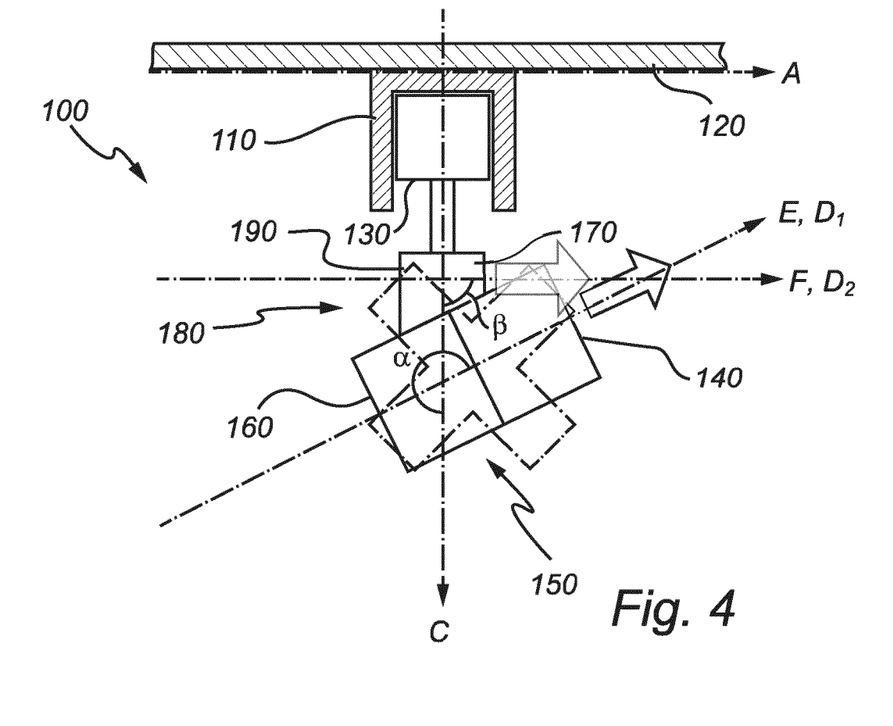
FIG. 4 is a schematic view of a track lighting system according to FIG. 1, with a blocking mechanism configured to avoid the first housing blocking the collimated second LED light.

FIG. 4 is a schematic view of a track lighting system 100 according to an exemplifying embodiment of the present invention. Regarding the features and/or functions of the track lighting system 100, it is referred to FIG. 1 for an increased understanding. The track lighting system 100 further comprises a blocking mechanism configured to avoid the first housing 150 blocking the collimated second LED light, as indicated by the schematic cross. Hence, the emission beam of the collimated second LED light may radiate unhindered relative blockage from the first housing 150.

Figure 5:
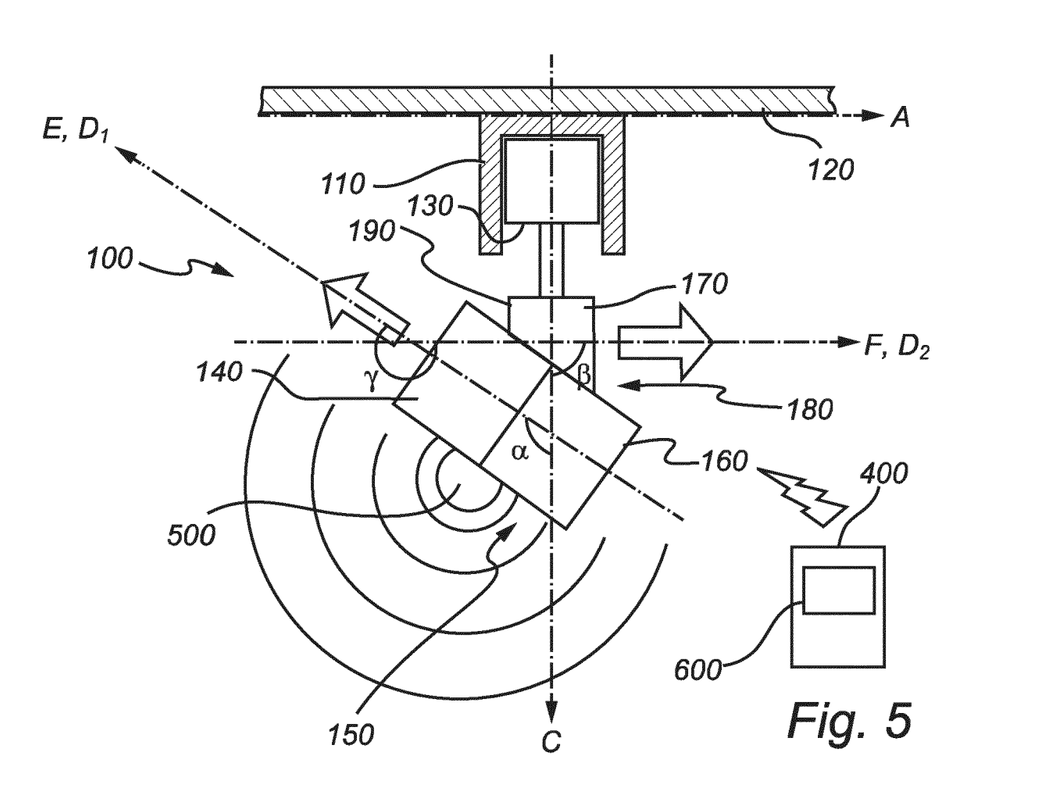
FIG. 5 is a schematic view of a track lighting system according to FIG. 1, with a sensor for detecting objects and/or persons, and a control unit coupled with the sensor wherein the control unit is configured to control the second LED light source.

FIG. 5 is a schematic view of a track lighting system 100 according to an exemplifying embodiment of the present invention. Regarding the features and/or functions of the track lighting system 100, it is referred to FIG. 1 for an increased understanding.

According to the arrangement of FIG. 5, a projection, P, of the first main direction, $D_1$, in the plane, A, and the second main direction, $D_2$, may be parallel, and wherein the first main direction, $D_1$, may form a third angle, γ, with the second main direction, $D_2$. Hence, the first main direction, $D_1$, in the plane, A, and the second main direction, $D_2$, may lie in a same plane, G (not shown), whereas the plane, G, is perpendicular to the plane, A. According to this example, wherein the track lighting system 100 is mounted to a ceiling via the power track 110, the (instantaneous) orientation of the track lighting system 100 as exemplified results in an emission of the first LED light in the first main direction, $D_1$, obliquely to the ceiling, and an emission of the second LED light in the second main direction, $D_2$, parallel to the ceiling.

Consequently, the arrangement of FIG. 5 results in that the emission of the first LED light in the first main direction, $D_1$, and the emission of the second LED light in the second main direction, $D_2$, lies in the same plane, G.

The track lighting system 100 further comprises a control unit 400 configured to control the second LED light source 170. In addition, the track lighting system 100 further comprises a sensor 500, wherein the sensor 500 is configured to detect an object and/or a person. In case an object/a person is detected, the sensor 500 may generate a sensor signal and send the generated signal to the control unit 400, whereas the control unit 400 is configured to control the second LED light source 170 based on the sensor signal received from the sensor 500. An example regarding the control from the control unit 400 is that if an object and/or a person is detected in the emission beam of the second light source 170, the control unit 400 turns off the second LED light source 170.

The track lighting system 100 further comprises a user interface 600 configured to control the first LED light source 140 in regard to e.g. increasing or decreasing the luminosity of the first LED light source 140. Thus, the user interface 600 provides a way for a user to interact with the first LED light.

The person skilled in the art realizes that the present invention by no means is limited to the preferred embodiments described above. On the contrary, many modifications and variations are possible within the scope of the appended claims. For example, one or more of the power track 110, the first and second housings, 150, 180, etc., may have different shapes, dimensions and/or sizes than those depicted/described.

The invention claimed is:

1. A track lighting system, comprising
 a power track being connectable to an electric supply and arranged to be mountable to a surface in a mounting direction, B, said mounting direction, B, being towards and orthogonal to said surface and
 a first light-emitting diode, LED, module being electrically and mechanically connectable to the power track, and wherein the first LED module comprises
 a first LED light source arranged to emit first LED light,
 a first housing, wherein the first housing at least partially encloses the first LED light source, and wherein the first housing comprises a first collimator having a first principal axis, E, and arranged to collimate the first LED light in a first main direction, $D_1$,
 a second LED light source arranged to emit second LED light, wherein the second LED light is different from the first LED light,
 a second housing, wherein the second housing at least partially encloses the second LED light source, wherein the second housing comprises a second collimator having a second principal axis, F, and arranged to collimate the second LED light in a second main direction, $D_2$,
 wherein the first collimator is tiltable with respect to a normal, C, of a plane, A, wherein the normal, C, is in an opposite direction to the mounting direction, B, such that the first principal axis, E, forms a first angle, α, with respect to the normal, C,
 wherein the second principal axis, F, of the second collimator is fixed with respect to tilt at a second angle, β, with respect to the normal, C, and
 wherein the track lighting system further comprising a blocking mechanism configured to avoid the first housing blocking the collimated second LED light.

2. The track lighting system according to claim 1, wherein the second angle, β, is between 70° and 110°, preferably between 80° and 100° and most preferably between 85° and 95°.

3. The track lighting system according to claim 1, wherein the second collimator is arranged such that the second principal axis, F, is arranged perpendicular to the normal, C.

4. The track lighting system according to claim 1, wherein at least one of the first collimator and the second collimator is rotatably arranged around the normal, C.

5. The track lighting system according to claim 4, further comprising a locking mechanism configured to lock an orientation of the second collimator around the normal, C.

6. The track lighting system according to claim 1, wherein the first LED light is white light having a correlated color temperature, CCT, in a range from 2000 to 8000 K and a color rendering index, CRI, of at least 70.

7. The track lighting system according to claim 1, wherein the second LED light is at least one of violet and ultraviolet, UV, light.

8. The track lighting system according to claim 7, wherein the second LED light is ultraviolet C, UVC, light.

9. The track lighting system according to claim 1, wherein a projection, P, of the first main direction, $D_1$, in the plane, A, and the second main direction, $D_2$, are parallel, and wherein the first main direction, $D_1$, forms a third angle, γ, with the second main direction, $D_2$.

10. The track lighting system according to claim 1, wherein the collimated first LED light has a first full width at half maximum, $FWHM_1$, and the collimated second LED light has a second full width at half maximum, $FWHM_2$, wherein $FWHM_1 > FWHM_2$.

11. The track lighting system according to claim 10, wherein $FWHM_2 < 5°$ in a direction perpendicular to the normal, C.

12. The track lighting system according to claim 1 further comprising
 a control unit configured to control the second LED light source, and
 at least one sensor coupled to the control unit, wherein the at least one sensor is configured to detect at least one of at least one object and at least one person, and, in case at least one of the at least one object and the at least one person is detected, to generate a sensor signal and send the generated signal to the control unit, wherein the control unit is configured to control the second LED light source based on the sensor signal received from the at least sensor.

13. The track lighting system according to claim 1, further comprising a user interface configured to control only the first LED light source.

14. The track lighting system according to claim 1, further comprising
 at least one second light-emitting diode, LED, module being electrically and mechanically connectable to the power track, and wherein the at least one second LED module comprises
 a third LED light source arranged to emit third LED light,
 a third housing, wherein the third housing at least partially encloses the third LED light source, and wherein the third housing comprises a third collimator arranged to collimate having a third principal axis, E, and arranged to collimate the third LED light in a third main direction, $D_3$,
 a fourth LED light source arranged to emit fourth LED light, wherein the fourth LED light is different from the first LED light, a fourth housing, wherein the fourth housing at least partially encloses the fourth LED light source, wherein the fourth housing comprises a fourth collimator having a fourth principal axis, F, and arranged to collimate the fourth LED light in a fourth main direction, $D_4$, wherein the third collimator is tiltable with respect to a normal, C, of a plane, A, wherein the normal, C, is in an opposite direction to the mounting direction, B, such that the third principal axis, E, forms a first angle, $\alpha$, with respect to the normal, C, wherein the fourth principal axis, F, of the fourth collimator is fixed with respect to tilt at a second angle, $\beta$, with respect to the normal, C, wherein the third LED light is white light having a correlated color temperature, CCT, in a range from 2000 to 8000 K and a color rendering index, CRI, of at least 70, wherein the fourth LED light is at least one of violet and ultraviolet, UV, light, and wherein a projection, P, of the third main direction, $D_3$, in the plane, A, and the fourth main direction, $D_4$, are parallel, and wherein the third main direction, $D_3$, forms a third angle, $\gamma$, with the fourth main direction, $D_4$.

* * * * *